(12) United States Patent
Ryan et al.

(10) Patent No.: US 9,669,190 B2
(45) Date of Patent: Jun. 6, 2017

(54) SELECTIVELY POSITIONABLE CATHETER CUFF

(71) Applicant: Cook Medical Technologies LLC, Bloomington, IN (US)

(72) Inventors: Olivia J. Ryan, Louisville, KY (US); Melissa R. Taylor, Dayton, OH (US); Steven Hough, LaGrange, KY (US); Clark Leiter, Bloomington, IN (US); Creasy Clauser, Crawfordsville, IN (US); Katherine Dostal, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 614 days.

(21) Appl. No.: 14/079,161

(22) Filed: Nov. 13, 2013

(65) Prior Publication Data

US 2014/0148788 A1    May 29, 2014

Related U.S. Application Data

(60) Provisional application No. 61/730,550, filed on Nov. 28, 2012.

(51) Int. Cl.
*A61M 25/04* (2006.01)
*A61L 29/14* (2006.01)
(Continued)

(52) U.S. Cl.
CPC .......... *A61M 25/04* (2013.01); *A61L 29/005* (2013.01); *A61L 29/085* (2013.01); *A61L 29/14* (2013.01)

(58) Field of Classification Search
CPC .......... A61M 25/04; A61M 2025/0286; A61M 2025/0213; A61M 2025/0266; A61M 25/0017; A61M 25/0029
See application file for complete search history.

(56) References Cited

U.S. PATENT DOCUMENTS 4,278,092 A * 7/1981 Borsanyi .............. A61M 1/285
                                                128/DIG. 26
4,405,313 A   9/1983 Sisley et al.
(Continued)

FOREIGN PATENT DOCUMENTS

EP        0 865 799 A2   9/1998

*Primary Examiner* — Aarti B Berdichevsky
(74) *Attorney, Agent, or Firm* — Woodard, Emhardt, Moriarty, McNett & Henry LLP (57) ABSTRACT

Devices and methods for securing a catheter with the body of a patient are generally disclosed. In particular, selectively positionable cuffs and methods for attaching selectively positionable cuffs to long-term tunneled catheters are disclosed. In one embodiment, a slidable, selectively-positionable cuff comprises an adhesive on a foldable tab. In another embodiment, a slidable, selectively positionable cuff comprises an activatable adhesive that is convertible from a nonadherent state to an adherent state beneath the skin of the patient. Additionally, the present disclosure teaches a wrappable sheet comprising a harvested extracellular matrix with an adhesive positioned on a side thereon and arranged to be adhered to the surface of a catheter so as to form a cuff. Methods of securing and/or positioning a cuff on a catheter, kits, and other embodiments are disclosed.

24 Claims, 6 Drawing Sheets

(51) Int. Cl.
*A61L 29/00* (2006.01)
*A61L 29/08* (2006.01)

(56) References Cited

U.S. PATENT DOCUMENTS

| | | | | |
|---|---|---|---|---|
| 4,676,782 | A * | 6/1987 | Yamamoto | A61M 39/0247 604/175 |
| 4,902,508 | A * | 2/1990 | Badylak | A61L 27/3629 424/423 |
| 5,053,023 | A * | 10/1991 | Martin | A61M 5/1582 604/43 |
| 5,308,338 | A * | 5/1994 | Helfrich | A61M 1/285 604/175 |
| 5,554,389 | A * | 9/1996 | Badylak | A61K 35/22 424/558 |
| 5,599,311 | A * | 2/1997 | Raulerson | A61M 25/02 604/174 |
| 5,830,184 | A * | 11/1998 | Basta | A61M 25/04 604/104 |
| 5,833,664 | A | 11/1998 | Seare, Jr. | |
| 5,993,844 | A * | 11/1999 | Abraham | A61K 35/12 424/422 |
| 6,033,382 | A | 3/2000 | Basta | |
| 6,099,567 | A * | 8/2000 | Badylak | A61L 27/3604 424/551 |
| 6,206,931 | B1 * | 3/2001 | Cook | A61L 2/0088 523/113 |
| 6,342,120 | B1 * | 1/2002 | Basta | A61M 25/04 156/242 |
| 6,730,096 | B2 * | 5/2004 | Basta | A61M 25/04 606/108 |
| 7,137,968 | B1 | 11/2006 | Burrell et al. | |
| 7,166,120 | B2 | 1/2007 | Kusleika | |
| 7,247,138 | B2 | 7/2007 | Reghabi et al. | |
| 7,722,571 | B2 | 5/2010 | Bierman et al. | |
| 7,753,889 | B2 | 7/2010 | Rosenberg | |
| 7,955,307 | B2 | 6/2011 | Bierman et al. | |
| 8,100,863 | B2 * | 1/2012 | Moehle | A61M 25/0009 604/175 |
| 8,535,265 | B2 * | 9/2013 | Burnett | A61M 16/04 128/207.15 |
| 8,636,700 | B2 * | 1/2014 | Moehle | A61M 25/0009 604/175 |
| 2002/0032411 | A1 * | 3/2002 | Basta | A61M 25/00 604/174 |
| 2004/0186461 | A1 | 9/2004 | DiMatteo | |
| 2004/0199110 | A1 * | 10/2004 | Basta | A61M 25/04 604/104 |
| 2005/0070882 | A1 | 3/2005 | McBride | |
| 2005/0107868 | A1 * | 5/2005 | Nakayama | A61L 27/38 623/1.39 |
| 2006/0079845 | A1 | 4/2006 | Howard et al. | |
| 2006/0135946 | A1 | 6/2006 | Moehle et al. | |
| 2006/0200111 | A1 * | 9/2006 | Moehle | A61M 25/0009 604/539 |
| 2007/0112334 | A1 * | 5/2007 | Porter | A61F 2/0077 604/539 |
| 2007/0149949 | A1 * | 6/2007 | Porter | A61F 2/0077 604/523 |
| 2008/0045894 | A1 | 2/2008 | Perchik et al. | |
| 2008/0312599 | A1 | 12/2008 | Rosenberg | |
| 2009/0171295 | A1 * | 7/2009 | Porter | A61F 2/0077 604/175 |
| 2009/0292248 | A1 | 11/2009 | Schon et al. | |
| 2010/0049116 | A1 | 2/2010 | Kerr | |
| 2010/0174240 | A1 | 7/2010 | Wells et al. | |
| 2010/0241084 | A1 | 9/2010 | Rosenberg | |
| 2011/0146691 | A1 * | 6/2011 | Burnett | A61M 16/04 128/207.15 |
| 2012/0016312 | A1 | 1/2012 | Brown et al. | |
| 2012/0116323 | A1 * | 5/2012 | Moehle | A61M 25/0009 604/264 |
| 2014/0142510 | A1 * | 5/2014 | Moehle | A61M 25/0009 604/175 |
| 2014/0276606 | A1 * | 9/2014 | Cavett | A61M 25/04 604/508 |

* cited by examiner

SELECTIVELY POSITIONABLE CATHETER CUFF

CROSS-REFERENCE TO RELATED APPLICATIONS

This application claims the benefit of U.S. Provisional Application No. 61/730,550, filed Nov. 28, 2012, which is hereby incorporated by reference in its entirety.

FIELD OF THE INVENTION

The present invention pertains generally to the field of catheter cuffs.

BACKGROUND

A catheter, shunt, drainage tube and the like, generally referred to herein as a catheter, can be used to obtain percutaneous access to a location within the body of a patient. In some instances, the catheter, such as a central venous catheter (CVC) or a peripherally inserted central catheter (PICC), may be tunneled under the skin between a skin exit site and a vessel entry site. Depending on the application, the catheter may be left in place for a short period of time, such as hours or days, and/or a longer period of time, such as more than a month. For example, a long term tunneled catheter may be used for drug administration, chemotherapy, blood transfusions, aspirations, and/or delivery of total parenteral nutrition (TPN), to name just a few non-limiting examples.

Some long-term tunneled catheters have a cuff that is meant to stabilize the catheter and avoid potentially life threatening infection. In many cases, the cuff is fixed at a predetermined position on the catheter shaft by the manufacturer. For example, the cuff may be glued to the catheter and/or retained in position by protrusions on the outer surface of the catheter. To obtain proper positioning of the catheter and the cuff, clinicians often cut off a portion of the catheter so that the length between the cuff and distal tip (i.e., the "cuff-to-tip length") is appropriate for a specific patient's anatomy. Unfortunately, cutting the catheter in this way may remove a specialized tip, such as a specific material or shape. Alternatively or additionally, cutting the catheter may alter expected flow dynamics and/or result in edges that may injure the patient and/or lead to undesirable clotting. Additionally, the step of cutting the catheter adds time and effort to the placement of the long-term tunneled catheter. Thus, new catheter cuff arrangements and methods are desired.

SUMMARY

The present disclosure pertains generally to catheter cuffs. In some aspects, methods of adhering a cuff on a catheter and arrangements of movable cuffs that are selectively positionable along a length of a catheter are described. In one embodiment, the present disclosure teaches a method of adhering a cuff on a catheter comprising: advancing a distal tip of the catheter through the body of a patient to a target site beneath the skin of the patient; selectively positioning a portion of a selectively positionable cuff having an activatable adhesive thereon on a portion of the catheter arranged for positioning beneath the skin when the distal tip is at the target site; and activating the activatable adhesive so as to adhere the cuff to the catheter and resist movement of the cuff along a length of the catheter. In some instances, the method further comprises positioning a portion of the cuff beneath the skin of the patient prior to activating the activatable adhesive. Additionally or alternatively, the cuff can be selectively positionable around a portion of the catheter and comprise an activatable adhesive that is convertible from a nonadherent state to an adherent state; wherein in the nonadherent state the cuff is slidable along a length of the catheter from a first position to a second position; and wherein in the adherent state the activatable adhesive adheres the cuff to the catheter to resist movement of the cuff along a length of the catheter.

In another embodiment, the present disclosure teaches a kit, comprising: a catheter; a cuff selectively positionable around a portion of the catheter and comprising an activatable adhesive that is convertible from a nonadherent state to an adherent state; wherein in the nonadherent state the cuff is slidable along a length of the catheter from a first position to a second position; and wherein in the adherent state the activatable adhesive adheres the cuff to the catheter to resist movement of the cuff along a length of the catheter. In some instances, the activatable adhesive is activatable by interaction with light. Additionally or alternatively, the cuff can comprise a foldable adhesive tab. In some embodiments, the cuff comprises harvested extracellular matrix.

In one aspect, the present disclosure provides a cuff comprising: a cuff body arranged to be slidable along a portion of a catheter shaft; a pivotable portion pivotably associated with the cuff body and arranged to pivot from a first position remote from the catheter shaft to a second position proximate to the catheter shaft; and an adhesive positioned on the pivotable portion and arranged to adhere the pivotable portion to the catheter shaft when the pivotable portion is in the second position. In some instances, the positionable portion comprises a foldable tab. Additionally or alternatively, the cuff body can comprise a harvested extracellular matrix.

Additionally, in another aspect, the present disclosures provides a cuff comprising: a wrappable sheet having a first side and a second side, comprising a harvested extracellular matrix, and arranged to be wrapped around a portion of a catheter shaft; and the first side comprising an adhesive; wherein the first side faces the catheter shaft when the wrappable sheet is wrapped around a portion of a catheter shaft. In some embodiments, the wrappable sheet is arranged to be wrapped in multiple layers around the catheter shaft. Additionally or alternatively, the cuff can further comprise a layer coupling member positioned on the second side and arranged to couple adjacent layers of the wrappable sheet. In some instances, the second layer coupling member comprises an adhesive, which can comprise an activatable adhesive.

Further forms, objects, features, aspects, benefits, advantages, and embodiments of the present invention will become apparent from a detailed description and drawings provided herewith.

DESCRIPTION OF THE ILLUSTRATED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

For simplicity, the following embodiments will be discuss with reference to long-term tunneled catheters, in some instances, catheters accessing the subclavian vein and tunneled through the chest of a patient. However, it is not intended that the present disclosure be limited to such. As will be appreciated by one of ordinary skill in the art, the present disclosure pertains to catheters, shunts, drainage tubes and the like, generally referred to herein as catheters. It will also be appreciated that the present disclosure is not limited to long-term tunneled catheters that are tunneled through the chest of a patient but that it can also apply to short-term tunneled catheters positioned in other locations in the body of a patient.

Figure 1:
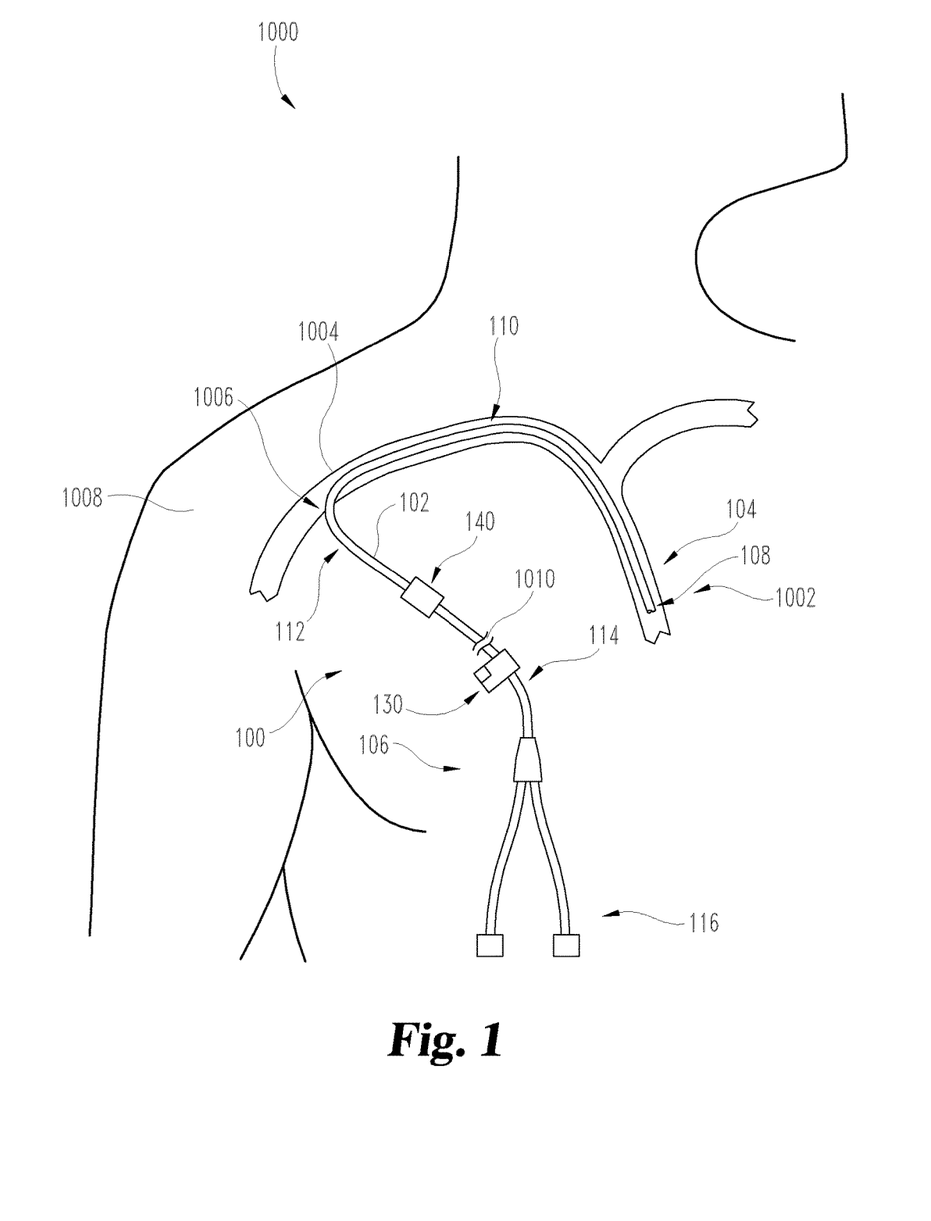
FIG. 1 illustrates a front view of the body of a patient with a long-term tunneled catheter.

As illustrated in FIG. 1, an exemplary long-term central catheter, such as catheter 100, comprises a catheter shaft 102 extending from a distal end region 104 positioned within the body of a patient to a proximal end region 106 positioned externally of the patient. Distal end region 104 comprises a distal tip 108 that, in some instances, comprises a specialized tip such a specialized material and/or a specialized shape.

As illustrated in FIG. 1, when implanted distal tip 108 of tunneled catheter 100 is positioned at a target site 1002 within body 1000 of a patient, the portion of catheter 100 positioned proximally of distal tip 108 extends through a vessel 1004 of the patient, such as the subclavian vein. Catheter shaft 102 then exits vessel 1004 at vessel entry site 1006 and passes underneath skin 1008 until exiting out of skin exit site 1010, so as to be exposed from body 1000 of the patient.

When catheter 100 is positioned with body 1000, as illustrated in FIG. 1, catheter 100 has a vessel portion 110 that extends through vessel 1004, a tunneled portion 112 that extends under skin 1008 of patient from vessel entry site 1006 to skin exit site 1010, and an exposed portion 114 that is positioned outside the body 1000. In some instances, catheter 100 has connectors 116 positioned in proximal end region 106 and arranged to fluidly connect catheter 100 with one or more external devices such as syringes, pumps and/or other perfusion devices.

Catheter 100, in some instances, has a cuff 140 positioned around tunneled portion 112 of catheter shaft 102. Cuff 140 stabilizes catheter 100 in position in body 1000 of the patient by resisting movement of catheter 100 when subjected to pulling and other stresses, so that distal tip 108 remains at target site 1002. Additionally and/or alternatively, cuff 140 can aid in preventing infection by promoting tissue growth around skin exit site 1010 and into cuff 140 so as to create a seal around catheter shaft 102 that reduces infection risk and further increases stability of catheter 100.

Catheter 100 may be inserted into vessel 1004 and/or tunneled under skin 1008 in any number of methods. In some instances, a medical professional may use the Seldinger technique to obtain access into vessel 1004. For example, a trocar may be used to puncture skin 1008 and a wall of vessel 1004 so as to gain access to the lumen of vessel 1004. A guide wire may then be advanced through the lumen of the trocar and into the lumen of vessel 1004. In some instances, the guide wire is advanced through vessel 1004 towards target site 1002. Once the guide wire is in the desired position, the trocar may be withdrawn over the guide wire from vessel entry site 1006.

With the guide wire positioned within the lumen of vessel 1004 and extending to target site 1002, a medical professional may advance catheter 100 along the guide wire towards target site 1002. In some instances, one or more dilators are passed over the surface of the guide wire to enlarge the opening in the skin and/or the vessel for receiving the catheter. When distal end region 104 of catheter 100 is in the desired position at target site 1002, the guide wire can be removed from the lumen of catheter 100.

Prior to and/or after advancing a portion of the catheter 100 over the guide wire, the medical professional can tunnel a portion of catheter 100 beneath skin 1008 of a patient. For example, the medical professional may use a tunneling device to push and/or pull portions of catheter 100 beneath the skin 1008 from the vessel entry site 1006 to a skin exit site 1010 or vice-versa, so as to have exposed portions of catheter 100 extending from skin exit site 1010 and vessel entry site 1006. If not already advanced, distal end region 104 of catheter 100 may then be advanced to position distal tip 108 at target site 1002.

In some instances, an external marker 130 can be attached to the outer surface of catheter 100 so as to indicate the depth at which catheter 100 is inserted when distal tip 108 is positioned at target site 1002, such as to aid in the positioning of cuff 140. For example, a portion of catheter 100 may be tunneled underneath skin 1008 of the patient and distal tip 108 positioned at target site 1002. External marker 130 may then be attached to the outer surface of catheter 100 at a location adjacent to and/or proximate to skin exit site 1010 to mark the portion of catheter 100 that extends through skin exit site 1010. Catheter 100 may then be withdrawn and cuff 140 positioned on the outer surface of tunneled portion 112 of catheter 100 distal of the position of external marker 130. After cuff 140 is positioned and/or adhered to catheter 100, catheter 100 may then be re-advanced into the patient until external marker 130 returns to its initial position adjacent to and/or proximate to skin exit site 1010 so as to position cuff 140 beneath skin 1008. The medical practitioner then can reconfirm that distal tip 108 of catheter 100 is at target site 1002, such as by using fluoroscopy and/or ultrasound.

In some embodiments, external marker 130 can remain in position on catheter 100 after cuff 140 positioned on and/or adhered to catheter 100 and placed beneath skin 1008 of the patient. For example, external marker 130 may remain in position until and/or after cuff 140 sufficiently retains catheter 100 in position, such as by tissue ingrowth, in body 1000 of the patient. In some instances, external marker 130 can be attached to skin 1008 of patient, such as by using an adhesive, to maintain the positioning of distal tip 108 or catheter 100 at target site 1002. Alternatively, external marker 130 may be configured for movement from a position adjacent to and/or proximate to skin 1008 or skin exit site 1010 to a position remote from skin 1008 or skin exit site 1010 so as to indicate to the patient or a medical practitioner that catheter 100 has migrated and distal tip 108 may no longer be in target site 1002 and/or that cuff 140 is not sufficiently retaining catheter 100 in position within the patient.

Figure 2:
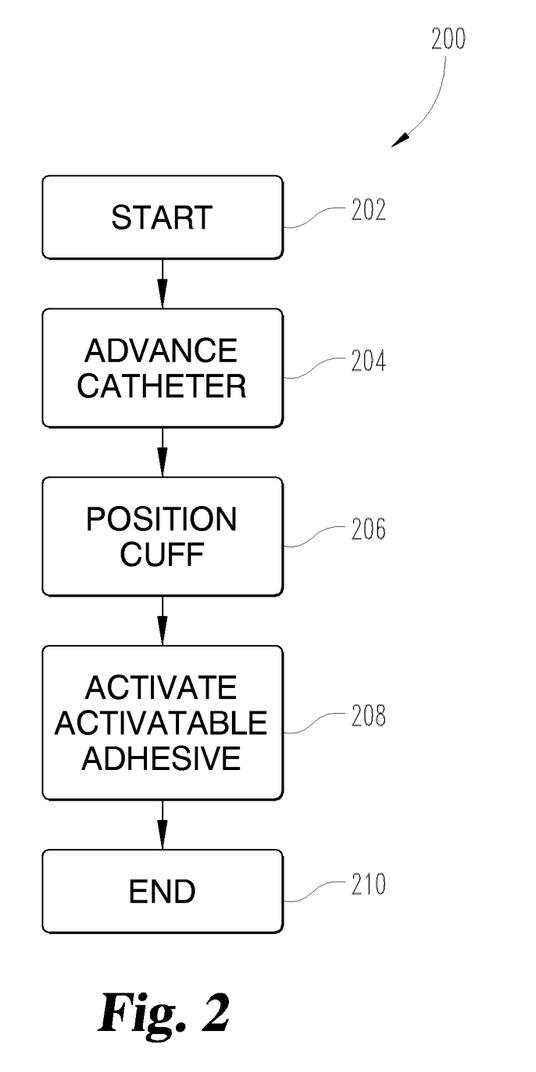
FIG. 2 is a flowchart illustrating a method of attaching a cuff to a catheter.
Figure 3:
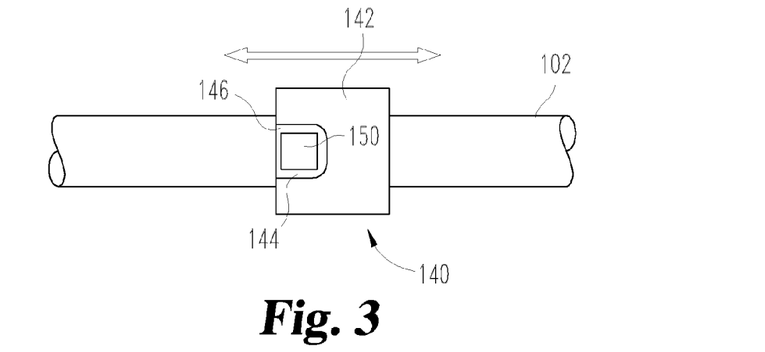
FIG. 3 illustrates a plan view of one embodiment of the present disclosure.
Figure 4:
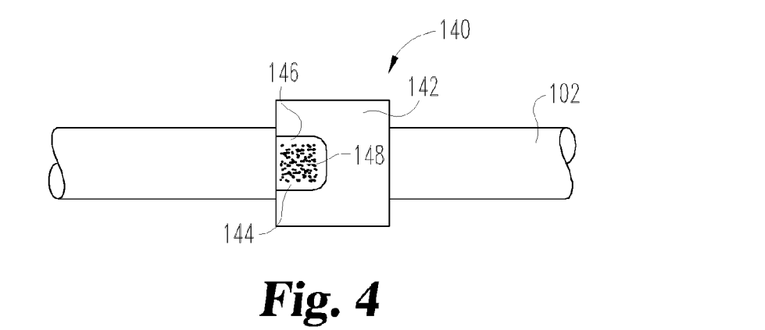
FIG. 4 illustrates a plan view of the embodiment of FIG. 3 with a protective film removed from the adhesive._
Figure 5:
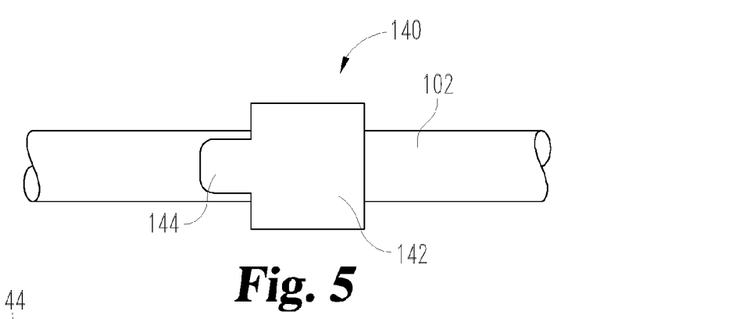
FIG. 5 illustrates a plan view of the embodiment of FIGS. 3 and 4 with the foldable tab folded into a second position.
Figure 6:
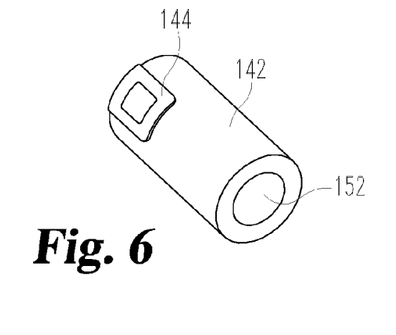
FIG. 6 illustrates a perspective view of the embodiment illustrated in FIGS. 3, 4, and 5.
Figure 7:
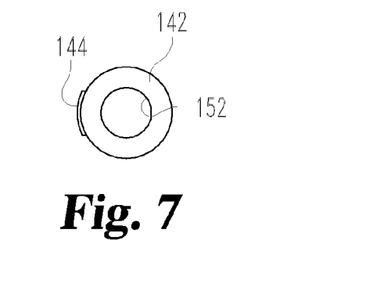
FIG. 7 illustrates a side elevational view of the embodiment illustrated in FIGS. 3, 4, 5, and 6.
Figure 8:
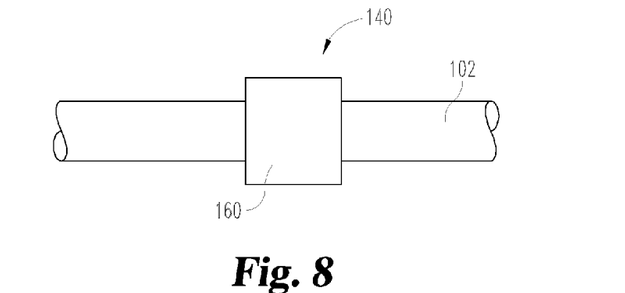
FIG. 8 illustrates a plan view of one embodiment of the present disclosure.
Figure 9:
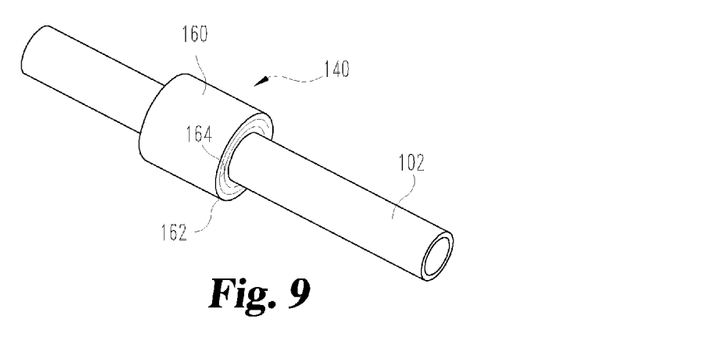
FIG. 9 illustrates a perspective view of the embodiment of FIG. 8.
Figure 10:
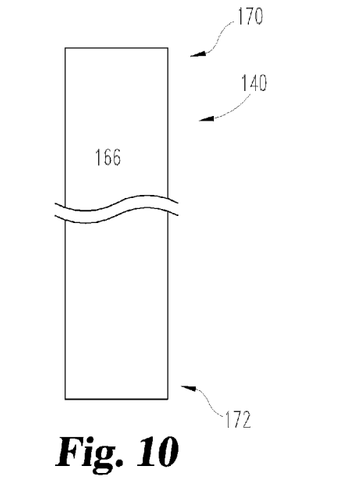
FIG. 10 illustrates a top plan view of the embodiment of FIGS. 8 and 9 in an unwrapped configuration.
Figure 11:
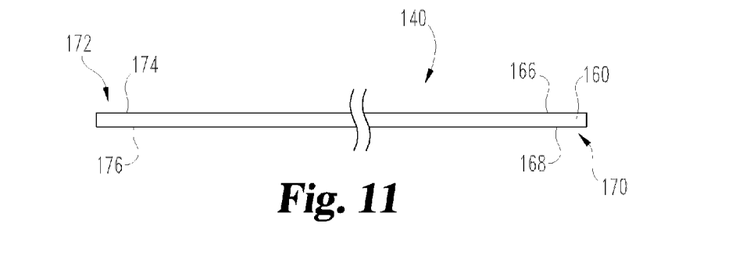
FIG. 11 illustrates a side elevational view of the embodiment of FIG. 10.

FIG. 2 shows a flow chart 200 that illustrates a method of adhering a cuff on a catheter. In stage 202, the catheter and cuff are obtained or otherwise provided in any number of manners. For instance, the catheter and cuff can be purchased from an outside vendor or provided by a medical device manufacturing company. In one example, the cuff is manufactured using an extracellular matrix material which is then packaged in a kit with a catheter and provided to a medical professional for use during a medical procedure. In some instances, a cuff and catheter assembly is packaged in a pre-assembled configuration with the cuff positioned around the catheter.

After stage 202 the medical professional obtains percutaneous access to a vessel, such as vessel 1004 illustrated in FIG. 1, that provides a path to target site 1002 within body 1000 of the patient. For example, a medical professional may use the Seldinger technique to obtain access to vessel 1004 and/or target site 1002. After the medical professional has obtained percutaneous access to vessel 1004, a guide wire may be advanced through vessel 1004 towards target site 1002 within body 1000 and catheter 100 tunneled underneath skin 1008 and advanced over the guide wire.

After stage 204, such as when distal tip 108 of distal end region 104 of catheter 100 is positioned at target site 1002, the medical professional may position cuff 140 along tunneled portion 112 of catheter 100. This may be done in a number of ways. For example, the medical professional may leave distal tip 108 of catheter 100 at target site 1002 and then slide cuff 140 along the catheter shaft 102 through skin exit site 1010 and around tunneled portion 112 of catheter 100, so as to position cuff 140 on tunneled portion 112. Alternatively, once distal tip 108 is positioned at target site 1002, the medical professional may withdraw catheter 100 a desired distance from underneath skin 1008 of the patient so as to expose a portion of tunneled portion 112 above the patient's skin 1008; position cuff 140 along a portion of catheter 100 withdrawn from beneath skin 1008, such as tunneled portion 112; and then readvance catheter 100 and cuff 140 towards target site 1002, so as to position cuff 140 beneath skin 1008 of the patient.

After stage 206, when cuff 140 is positioned in the desired location along catheter 100, such as along tunneled portion 112 of catheter 100, the medical professional may activate an activatable adhesive in stage 208 so as to adhere cuff 140 to the surface of catheter 100. As will be discussed below, activating the activatable adhesive can comprise converting the activatable adhesive from a nonadherent state to an adherent state. Additionally, or alternatively, activating the activatable adhesive may comprise curing the adhesive and/or causing the adhesive to adhere a cuff to a catheter. Activating the adhesive may occur in any number of steps. In some instances, activating the activatable adhesive comprises adding a second component to the activatable adhesive so as to harden or cure the adhesive. Similarly, in some embodiments, an energy source can be used to apply energy, such as ultraviolet (UV) light, to the activatable adhesive to cure the adhesive.

In some instances, the activatable adhesive does not significantly inhibit relative movement between the cuff and the catheter prior to the adhesive being activated. For example, the cuff and catheter may be slidably coupled to one another with the activatable adhesive in frictional contact with the catheter but not adhering the cuff to the catheter and preventing slidable movement there along prior to activation of the activatable adhesive. After activating the activatable adhesive, the cuff and catheter can be adherently coupled (e.g., adhered) to one another.

Advantageously, in some instances, cuff 140 can be adhered to a portion of catheter 100 beneath skin 1008 and/or external of body 100 of the patient. For example, the activatable adhesive on cuff 140 may be activated when cuff 140 is positioned on tunneled portion 112 beneath the skin 1008 and/or outside of skin 1008. In some instances, the activatable adhesive on cuff 140 is activated to adhere cuff 140 to tunneled portion 112 of catheter shaft 102 prior to inserting cuff 140 through skin exit site 1010. In other instances, the activatable adhesive is activated so as to adhere cuff 140 onto tunneled portion 112 of catheter 100 when tunneled portion 112 is positioned beneath skin 1008 of the patient. For example, the activatable adhesive can comprise a moisture cured adhesive that is activated upon interaction with interstitial fluid. Preferably, the medical professional has at least approximately determined the appropriate location at which to position cuff 140 along catheter 100 so as to have a suitable cuff-to-tip distance for target site 1002 prior to activating the activatable adhesive.

In some instances, the activatable adhesive can be activated and then the medical practitioner can remove and/or reposition cuff 140 for at least a period of time. For example, in some embodiments, the medical practitioner may reposition cuff 140 along catheter 100 for up to two (2) minutes after application of the activating energy or activating material that activates the activatable adhesive. In some instances, cuff 140 is positionable for a period between about 30 seconds to about two minutes. Once cuff 140 is adhered onto a portion of catheter 100, the process concludes in stage 210.

It should be understood that only a few exemplary methods were discussed above, but limitation to these few examples is not intended. For example, it is envisioned that the various stages described above can occur in a different order than described and/or illustrated herein. Moreover, various stages can be omitted or combined together so as to occur simultaneously. Other additional acts can be performed besides those described above. Moreover, the various acts can be performed in any number of manners. For instance, the medical practitioner may measure the distance between vessel entry site 1006 and target site 1002 to determine the minimum cuff-to-tip distance. As one example, the medical practitioner may measure and/or note the distance from vessel entry site 1006 to target site 1002. This would be the minimum cuff-to-tip distance. The medical practitioner may also measure and/or note the distance from vessel entry site 1006 to skin exit site 1010 and add that to the minimum cuff-to-tip distance and/or measure the distance from target site 1002 to skin exit site 1010. This would be the maximum cuff-to-tip distance. Using these two distance measurements and/or notes, the medical practitioner may then position a cuff, such as cuff 140, along a length of the catheter between the maximum and minimum cuff-to-tip distances so that when the tunneled catheter assembly is implanted in the body of a patient, the cuff is positioned between vessel entry site 1006 and skin exit site 1010. Advantageously, the appropriate cuff-to-tip distance can be obtained by positioning the cuff, without requiring cutting the distal tip of the catheter.

Various types of adhesives may be used to adhere cuff 140 to catheter 100. In some instances, it may be preferred that the one or more adhesives used to adhere cuff 140 and catheter 100 are medical-grade adhesives. In some embodiments it may be preferred to use an activatable adhesive. For instance, activatable adhesives can comprise moisture cured adhesives, enzyme cured adhesives, and multi-component adhesives which harden by the mixture of two or more components which chemically react with one another. For example, the chemical reaction may cause polymers to cross link into acrylics, urethanes, and/or epoxies. Some examples of multi-component adhesives include polyester resin mixed with polyurethane resin, polyols mixed with polyurethane resin, and acrylic polymers mixed with polyurethane resins. Individually, the components of multi-component adhesives are typically not adhesive by nature. The components show adhesion, however, after being mixed together and cured.

In some instances, an activatable adhesive comprises one-part, reactive-type adhesive that hardens via a chemical reaction with an external energy source such as ultraviolet (UV) light and/or heat. When the external energy source is applied to the one-part, reactive-type adhesive a chemical reaction occurs and the activatable adhesive adheres cuff 140 and catheter 100 together.

Some embodiments can comprise non-reactive type adhesives, such as those that harden by drying, and/or adhere by pressure, contact, and/or by heat. For example, pressure sensitive adhesives like tape, such as medical tape, adhere by applying pressure to couple the adhesive with the surface of the body being adhered. Pressure sensitive adhesives may be either permanent or removable-type adhesives and can be manufactured in a liquid or solid form. Hot adhesives comprise the heating and liquefaction and subsequent solidification of thermal plastics. One example of a hot adhesive is ethylene-vinyl acetate, which, for example, is melted into a liquid form and then solidified to adhere bodies together.

As will be appreciated by one of ordinary skill of the art, many different types of adhesive such as reactive and/or non-reactive can be used to join or to adhere cuff 140 to catheter 100, but in some instances one type of adhesive may be preferable over another. For example, an activatable-type adhesive may be desired over a non-activatable adhesive in some instances. Similarly, a biocompatible and/or biodegradable adhesives may be desired for certain embodiments. As one non-limiting example, portions of cuff 140 and/or catheter shaft 102 may comprise a Vitralit® medical grade UV adhesive which is manufactured by Eurobond Adhesives Limited and is cured by application of UV light.

In some instances, such as when cuff 140 is to be adhered to catheter 100 beneath skin 1008 of the patient, a light-activated adhesive can be arranged to be activated by light having a wavelength sufficient to pass through the skin of the patient. For example, the light-activated adhesive may be arranged to convert from a nonadherent state to an adherent state upon the application of light having a wavelength between 400 and 800 nm.

In some embodiments, cuff 140 may be arranged to constrict and/or shrink around a portion of catheter 100 so as to increase the frictional resistance to slidable movement of cuff 140 along the surface of catheter 100. For example, a portion of cuff 140 may comprise a shrink-wrap material that upon heating shrinks and/or conforms to the surface of catheter 100. In some instances, cuff 140 and/or catheter 100 are adhered to one another by both increased frictional resistance due to a deformation of cuff 140 and an adhesive, such as an activatable adhesive.

In some instances, cuff 140 and/or portions of catheter 100 may be arranged to couple cuff 140 and catheter 100 upon the application and/or removal of heat. For example, portions of cuff 140 may have a lower melting temperature than portions of catheter 100. When cuff 140 is positioned in the desired location on tunneled portion 112, heat can be applied to catheter 100 and/or cuff 140 so as to melt a portion of cuff 140 along a surface of catheter 100, or vice-versa, so as to fixedly couple catheter 100 and cuff 140 to one another. In some embodiments, heat may be applied to melt portions of both catheter 100 and cuff 140 so as to fuse catheter 100 and cuff 140 together. As will be appreciated by one of ordinary skill in the art, heat may be applied to catheter 100 and/or cuff 140 in a number of ways such as by flowing warm and/or hot fluid through catheter 100, applying ultrasonic energy, and/or heating with a resistive heating element, to name just a few non-limiting examples.

FIGS. 3-7 illustrate one embodiment of cuff 140. In some instances cuff 140 comprises a cuff body 142 which is arranged to substantially surround catheter shaft 102. In some instance, a portion of cuff body 142 completely surrounds catheter shaft 102, e.g., extending around the entire periphery. In other instance, cuff body 142 does not extend completely around the periphery of catheter shaft 102.

Extending from cuff body 142 is a moveable portion such as foldable tab 144. Foldable tab 144 is moveable between a first position and a second position. Additionally or alternatively, the movable portion can comprise a pivotable portion that is pivotably associated with cuff body 142 and is arranged to pivot from a first position to a second position. In some instances, the first position is adjacent to the surface of cuff body 142 and/or remote from catheter shaft 102, and the second position is proximate to catheter shaft 102.

In some embodiments, an adhesive 148 is positioned on a first surface 146 of foldable tab 144. In some instances, adhesive 148 is covered by protective film 150 that may be removed so as to expose adhesive 148 on foldable tab 144 prior to adherence of cuff 140 to catheter shaft 102. After removal of protective film 150 from adhesive 148, foldable tab 144 may be folded from a first position to a second position in which first surface 146 faces catheter shaft 102 and adhesive 148 adheres cuff 140 to catheter shaft 102.

In some instances, cuff 140 is arranged to be slidably coupled with catheter shaft 102. For example, cuff 140 can comprise an inner surface 152 that defines an opening arranged for receiving a portion of catheter shaft 102 and slidably coupling cuff 140 to catheter shaft 102. In some embodiments of the present disclosure, inner surface 152 comprises an adhesive that is capable of adhering cuff 140 to catheter shaft 102 so as to prevent movement of cuff 140 along a length of catheter shaft 102. As mentioned above, adhesive 148 that can be positioned on foldable tab 144 and/or the adhesive positioned on inner surface 152 may comprise an activatable-type adhesive such as an adhesive activated by an external energy source and/or moisture. In some instances, adhesive 148 positioned on foldable tab 144 comprises a non-reactive type adhesive (e.g., pressure sensitive).

Advantageously, at least some of the above arrangements of cuff 140 can allow a medical practitioner to position cuff 140 around catheter shaft 102 with one hand. For example, a medical practitioner may remove protective film 150, grasp cuff 140, slide it along a length of catheter shaft 102 into position in tunneled portion 114, and then use a finger on his/her hand, such as a thumb, to move foldable tab 144 from a first position to a second position in which adhesive 148 adheres cuff 140 to catheter shaft 102.

Another embodiment of cuff 140 is illustrated in FIGS. 8-13. As illustrated, an elongated sheet may be rolled around catheter shaft 102 so as to form a cylindrical cuff 140 around catheter 100. In some instances, a cuff body 160 may form a series of layers such as layers 162 and 164 around catheter 100. In these instances, layers 162 and 164 of cuff 140 may couple to the surface of catheter shaft 102 and/or to one another. For example, layer 164 of cuff body 160 may have a first surface arranged for coupling cuff body 160 to catheter shaft 102. Additionally or alternatively, layer 162 may have a second surface arranged for coupling first layer 162 and second layer 164 to one another.

In some instances, portions of cuff body 160 may have different adhesives and/or coupling members positioned thereon. For example, a first end region 170 may have an activatable adhesive positioned on a first surface 166 for coupling cuff body 160 to catheter shaft 102 and/or a non-activatable type adhesive positioned on a second surface 168, such as for coupling first layer 162 of cuff body 160 to second layer 164 of cuff body 160.

In some instances a side of cuff body 160 may have different adhesives and/or different adherent properties along different portions of that side, such as portions along its length. For instance, first surface 166 of first end region 170 of cuff body 160 may have a different adhesive than third surface 174 of second end region 172. For example, first surface 166 of first end region 170 may have an adhesive arranged for adhering cuff body 160 to catheter shaft 102 while third surface 174 of second end region 172 may comprise an adhesive arranged to adhere portions of cuff body 160 to itself, such as adhering second layer 164 to first layer 162. In some embodiments, surfaces of cuff body 160 can be arranged to couple with each other and not with other surfaces. For example, third surface 174 may comprise a hook material and second surface 168 have a loop material, such as Velcro®.

In some instances, cuff body 160 may also have a fourth surface 176 that is free of an adhesive. Additionally or alternatively, one or more surfaces of cuff body 160, such as fourth surface 176, may be coated with a material arranged to promote the ingrowth of tissue, such as a growth hormone, to name one non-limiting example. In some instances, growth-promoting material is embedded in portions of cuff body 160 and/or positioned on internal surfaces of cuff body 160. For example, growth hormone may be positioned on the surfaces between layers of cuff body 160, such as surface 168 and/or surface 174 that can face one another when cuff 140 is wrapped around a catheter shaft 102 so as to promote tissue growth between layers at cuff 140.

Figure 12:
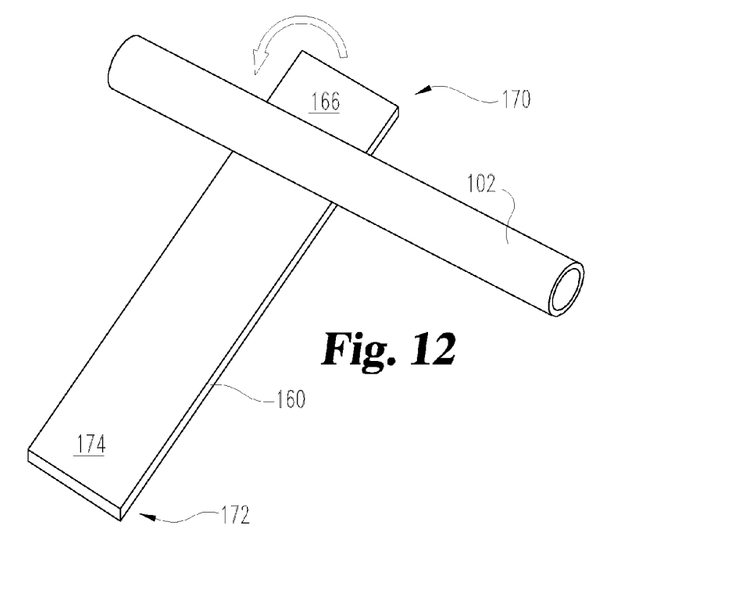
FIGS. 12 and 13 illustrate perspective views of one method of positioning, wrapping, and/or activating the activatable adhesive for the embodiment of FIGS. 8, 9, 10, and 11.
Figure 13:
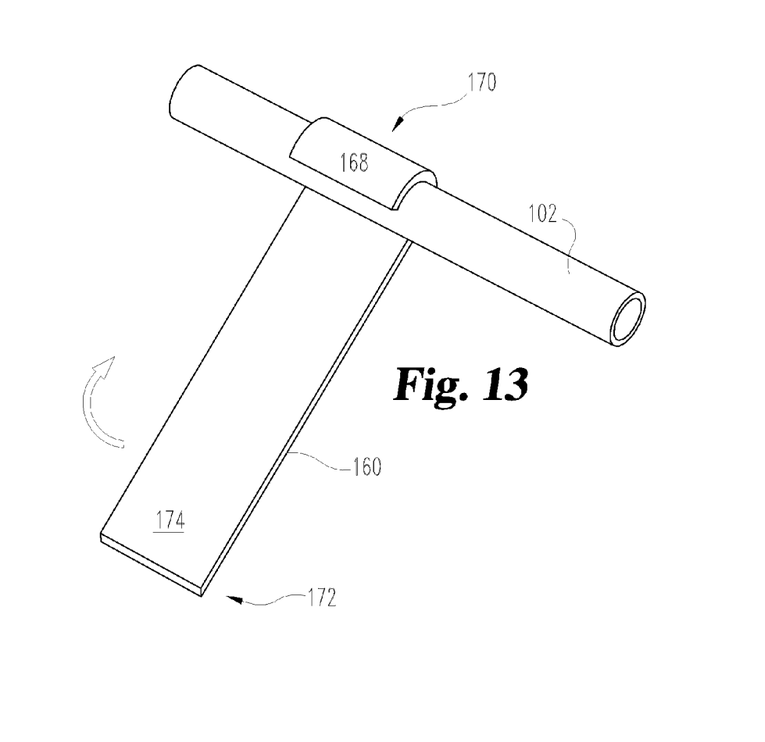

Cuff body 160 may be formed around catheter 100 in any number of ways, as will be appreciated by one of ordinary skill in the art. For example, as illustrated in FIGS. 12 and 13, cuff body 160 can comprise a rollable and/or wrappable sheet that may be rolled and/or wrapped around portions of catheter shaft 102 in one or more layers so as to form cuff 140 around catheter 100. In some instances, cuff body 160 may be wrapped around a portion of catheter 100, such as catheter shaft 102, starting from one end region, such as first end region 170, and working towards another end region, such as second end region 172. In other instances, cuff body 160 is wrapped around a portion of catheter 100 starting from a central portion of cuff body 160. For example, catheter shaft 102 may be positioned between the end regions 170 and 172 of cuff body 160 and the end regions 170 and 172 of cuff body 160 wrapped around catheter shaft 102 in opposing directions. As illustrated in FIGS. 12 and 13, first end region 170 can be wrapped around catheter shaft 102 in one direction and second end region 172 wrapped around catheter shaft 102 in an opposing direction. In some cases, one end region may be wrapped over another end region, such as second end region 172 being wrapped over first end region 170, so as to form multiple layers of cuff body 160.

In some instances, cuff body 160 can have a protective film and/or backing on the adhesive side that can be pulled off prior to use. In some instances, cuff 140 is provided by a manufacturer as a roll of cuff body 160. Additionally, or alternatively, a medical practitioner may then unroll portions of cuff body 160 from the provided roll and wrap portions of cuff body 160 around the desired location of catheter shaft 102. When the desired thickness and/or length of cuff 140 is wrapped around catheter shaft 102, a medical practitioner or surgical assistant may then cut and/or tear cuff body 160 between the wrapped portion and the portion in the provided roll.

Figure 14:
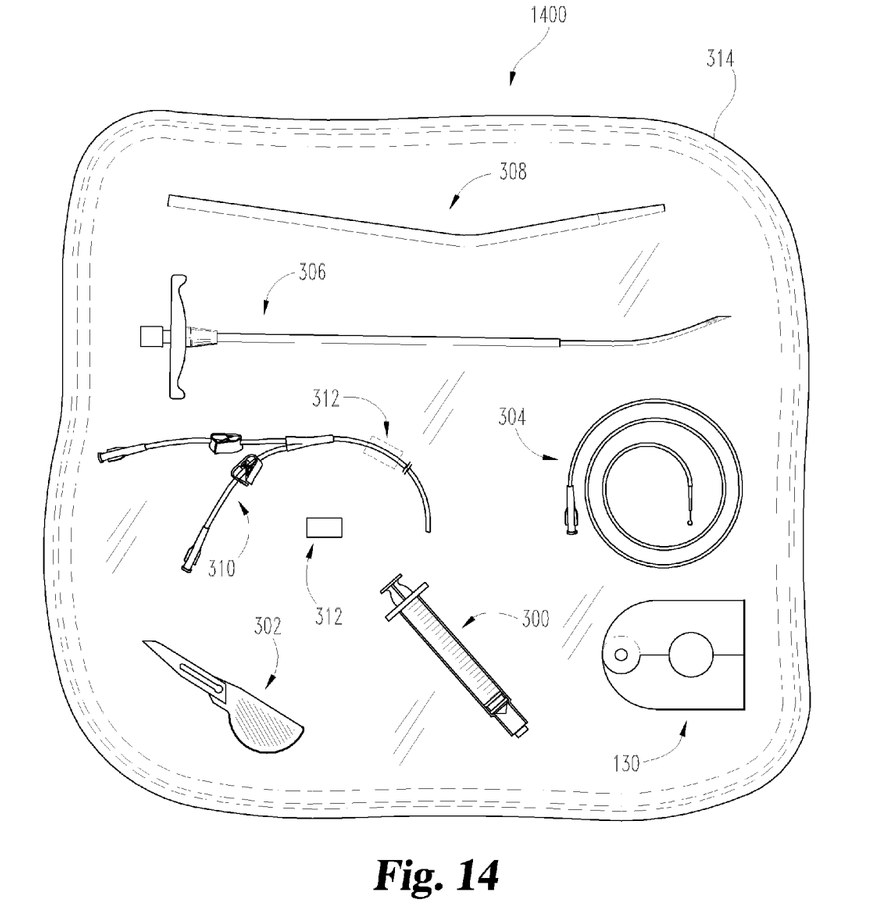
FIG. 14 illustrates one embodiment of a kit.

FIG. 14 illustrates one type of kit that may include a cuff and/or catheter arrangement, such as those described above, that may be useful to a medical practitioner. For example, a kit 1400 may include a syringe 300 and/or a disposable scalpel 302 which may be used to obtain access to a vessel 1004 through skin 1008 of a patient. The kit 1400 may also contain a guide wire 304 that, once access is obtained, a medical professional may advance through the incision site into vessel 1004 and towards target site 1002. Kit 1400 can also have a peel-away introducer sheath 306 that is advanceable over guide wire 304 so as to dilate the opening through skin 1008 and vessel 1004. In some embodiments, kit 1400 can comprise a tunneler 308 arranged to tunnel a catheter 310 beneath skin 1008 between skin exit site 1010 and vessel entry site 1006 before or after insertion of catheter 310 through the peel-away introducer sheath 306. A cuff 312 from kit 1400 can be positioned along the tunneled portion of catheter 310 and beneath skin 1008 of the patient and may be subsequently adhered to catheter 310 so as to achieve the desired cuff-to-tip distance without cutting the distal tip of catheter 310. To aid in convenience for the medical professional, items can be sterilely-sealed within packaging 314 so that the medical professional does not need to sterilize the devices prior to conducting a procedure.

In some embodiments, kit 1400 is provided with cuff 312 pre-mounted onto catheter 310. For example, cuff 312 may be positioned around a portion of catheter 310 and slidably positionable by a medical professional prior to adhering cuff 312 to catheter 310 so as to fix the cuff-to-tip distance in the immediately prior to, during, and or after positioning the distal tip of catheter 310 within the body of the patient. Alternatively, or additionally, cuff 312 may be provided in an unmounted arrangement within kit 1400. For example, for embodiments comprising a wrappable cuff, such as cuff 140 illustrated in FIGS. 8-13, cuff 312 may be provided in a roll and/or length of wrappable material.

Turning now to a discussion of materials that can be used in cuff 140, such materials can include any suitable biocompatible material. Generally, the material may include synthetic materials, such as a polyester felt, or reconstituted or naturally-derived collagenous materials. Such biocompatible materials that are at least bioresorbable will provide advantage in embodiments of the invention, with materials that are bioremodelable and promote cellular invasion and ingrowth providing particular advantage. Illustratively, remodelable materials may be used in this context to promote cellular growth.

Bioremodelable materials of the invention can be provided by collagenous extracellular matrix (ECM) materials possessing biotropic properties, including in certain forms angiogenic collagenous ECM materials. For example, suitable collagenous materials include ECM materials, such as submucosa, renal capsule membrane, dermal collagen, dura mater, pericardium, serosa, facia lata, peritoneum, or basement membrane layers including liver basement membrane. The preferred medical graft products of the invention will include submucosa, such as submucosa derived from a warm-blooded vertebrate. Suitable submucosa materials for these purposes include, for instance, intestinal submucosa, including small intestinal submucosa, stomach submucosa, urinary bladder submucosa, and uterine submucosa. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material used in the cuff embodiments described herein, such as cuff 140, can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Submucosa or other ECM materials can be derived from any suitable organ or other tissue source, usually sources containing connective tissues. The ECM materials processed for use in certain embodiments will typically include abundant collagen, most commonly being constituted of at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in embodiments of the invention will include significant amounts of such interspersed, non-collagenous solids that are readily ascertainable under light microscopic examination. Such non-collagenous solids can constitute a significant percentage of the dry weight of the ECM material in certain embodiments, for example at least about 1%, at least about 3%, and at least about 5% by weight in various embodiments of the invention.

The submucosa or other ECM material used in illustrative embodiments may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. In some instances, it is preferable for a portion of a cuff, such as the outer portion, to have an angiogenic character so as to further secure the cuff within the body of the patient and/or resist infection. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

As prepared and used, the submucosa material or any other ECM material may optionally retain and/or include growth factors or other bioactive components native to the source tissue. For example, the submucosa or other ECM material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in embodiments of the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto ECM material can include, for example, antibiotics and/or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after positioning of the ECM material around the catheter and/or within the patient.

Submucosa or other ECM material used in embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in aspects of the present invention.

While at least one embodiment has been illustrated and described in detail in the drawings and foregoing description, the same is to be considered as illustrative and not restrictive in character, it being understood that the preferred embodiment has been shown and described and that all changes, equivalents, and modifications that come within the spirit of the inventions defined by following claims are desired to be protected. It will be evident from the specification that aspects or features discussed in one context or embodiment will be applicable in other contexts or embodiments. All publications, patents, and patent applications cited in this specification are herein incorporated by reference as if each individual publication, patent, or patent application were specifically and individually indicated to be incorporated by reference and set forth in its entirety herein.

The invention claimed is:

1. A cuff, comprising:
a cuff body arranged to be slidable along a portion of a catheter shaft when the cuff body is positioned around the catheter shaft of a catheter having a distal tip;
a pivotable portion pivotably associated with said cuff body and arranged to pivot from a first position remote from the catheter shaft to a second position proximate to the catheter shaft when the cuff body is positioned around the catheter shaft; and
an adhesive positioned on a first side of said pivotable portion and arranged to adhere said pivotable portion to the catheter shaft when said pivotable portion is in said second position;
wherein the pivotable portion has a second side opposite said first side;
wherein when said cuff body is positioned around the catheter shaft in said first position, said second side of the pivotable portion faces said catheter shaft and said first side faces away from said catheter shaft; and
wherein when said cuff body is positioned around the catheter shaft in the said second position, said second side of the pivotable portion faces away from said catheter shaft and said first side faces said catheter shaft.

2. The cuff of claim 1, wherein:
said pivotable portion comprises a foldable tab.

3. The cuff of claim 1, wherein:
said cuff body comprises harvested extracellular matrix.

4. The cuff of claim 1, wherein:
said adhesive comprises an activatable adhesive.

5. A cuff, comprising:
a wrappable sheet having a first side and a second side, comprising a harvested extracellular matrix, and arranged to be wrapped around a portion of a catheter shaft of a catheter having a distal tip; and
said first side comprising an adhesive;
wherein said first side faces the catheter shaft when said wrappable sheet is wrapped around a portion of a catheter shaft; and
wherein said wrappable sheet defines a plurality of overlapping layers of harvested extracellular matrix material when wrapped around the catheter shaft.

6. The cuff of claim 5, wherein:
said adhesive comprises an activatable adhesive.

7. The cuff of claim 5, further comprising:
a layer coupling member positioned on said second side and arranged to couple adjacent layers of said wrappable sheet.

8. The cuff of claim 7, further comprising:
a layer coupling member positioned on said first side and arranged to couple to said layer coupling member positioned on said second side.

9. The cuff of claim 7, wherein:
said layer coupling member comprises an adhesive.

10. The cuff of claim 9, wherein:
said layer coupling member comprises an activatable adhesive.

11. A kit, comprising:
a catheter having a distal tip;
a cuff selectively positionable around a portion of said catheter and comprising an activatable adhesive that converts from a nonadherent state to an adherent state when activated while beneath skin of a patient;
wherein when said cuff is positioned around said catheter, said cuff is slidable along a length of said catheter from a first position to a second position when said activatable adhesive is in said nonadherent state and said activatable adhesive adheres said cuff to said catheter to resist movement of the cuff along a length of said catheter when said activatable adhesive is in said adherent state; and
wherein said activatable adhesive is activated by interaction with light having a wavelength sufficient to pass through the skin of the patient.

12. The kit of claim 11, wherein:
the cuff comprises harvested extracellular matrix.

13. The kit of claim 11, wherein
said catheter and said cuff are sterilely sealed within a package.

14. A method of adhering a cuff on a catheter, comprising:
advancing a distal tip of the catheter through the body of a patient to a target site beneath skin of the patient;
selectively positioning a portion of a selectively positionable cuff having an activatable adhesive thereon on a portion of the catheter arranged for positioning beneath the skin when the distal tip is at the target site;
positioning a portion of the cuff beneath the skin of the patient prior to activating the activatable adhesive; and activating the activatable adhesive so as to adhere the cuff to the catheter and resist movement of the cuff along a length of the catheter.

15. The method of claim 14, further comprising:
tunneling a portion of a catheter beneath the skin of a patient.

16. The method of claim 14, wherein:
the cuff is selectively positionable around a portion of the catheter and comprises an activatable adhesive that is convertible from a nonadherent state to an adherent state;
wherein in the nonadherent state the cuff is slidable along a length of the catheter from a first position to a second position; and
wherein in the adherent state the activatable adhesive adheres the cuff to the catheter to resist movement of the cuff along a length of the catheter.

17. The method of claim 14, wherein the cuff comprises:
a cuff body arranged to be slidable along a portion of a catheter shaft;
a pivotable portion pivotably associated with the cuff body and arranged to pivot from a first position remote from the catheter shaft to a second position proximate to the catheter shaft; and
an adhesive positioned on the pivotable portion and arranged to adhere the pivotable portion to the catheter shaft when the pivotable portion is in the second position.

18. The method of claim 14, wherein the cuff comprises:
a wrappable sheet having a first side and a second side, comprising a harvested extracellular matrix, and arranged to be wrapped around a portion of a catheter shaft; and
the first side comprising an adhesive;
wherein the first side faces the catheter shaft when the wrappable sheet is wrapped around a portion of the catheter shaft.

19. The method of claim 14, wherein:
activating the activatable adhesive comprises curing the activatable adhesive.

20. The method of claim 14, wherein:
positioning a portion of a cuff on a portion of the catheter comprises sliding a portion of the cuff along a length of the catheter.

21. The method of claim 14, wherein:
positioning a portion of a cuff on a portion of the catheter comprises wrapping a portion of the cuff around the catheter.

22. The method of claim 14, wherein:
the cuff comprises a harvested extracellular matrix.

23. The method of claim 14, wherein:
the activatable adhesive is activatable by interaction with light.

24. The method of claim 23, wherein:
the activatable adhesive is activatable by interaction with light that has passed through the skin of the patient.

* * * * *